US010852288B2

(12) United States Patent
Marshall et al.

(10) Patent No.: US 10,852,288 B2
(45) Date of Patent: Dec. 1, 2020

(54) OIL WELL GAUGING SYSTEM AND METHOD OF USING THE SAME

(71) Applicant: DWT Solutions, L.P., Bakersfield, CA (US)

(72) Inventors: Dan W. Marshall, Bakersfield, CA (US); Suzanne Griston Castrup, Bakersfield, CA (US)

(73) Assignee: Guide Valve USA Limited, Houston, TX (US)

( * ) Notice: Subject to any disclaimer, the term of this patent is extended or adjusted under 35 U.S.C. 154(b) by 308 days.

(21) Appl. No.: 16/151,287

(22) Filed: Oct. 3, 2018

(65) Prior Publication Data

US 2019/0049425 A1    Feb. 14, 2019

Related U.S. Application Data

(63) Continuation-in-part of application No. 15/166,910, filed on May 27, 2016, now abandoned.

(51) Int. Cl.
*G01N 33/28* (2006.01)
*E21B 49/08* (2006.01)
*E21B 47/10* (2012.01)

(52) U.S. Cl.
CPC ......... *G01N 33/2847* (2013.01); *E21B 47/10* (2013.01); *E21B 49/086* (2013.01); *G01N 33/2823* (2013.01); *E21B 49/0875* (2020.05)

(58) Field of Classification Search
CPC ... G01F 1/74; G01F 1/76; E21B 47/10; E21B 49/08; E21B 49/086; E21B 49/087; E21B 49/088; E21B 21/067; E21B 2049/085; G01N 33/2847

USPC ............ 73/861.04, 152.42; 702/13
See application file for complete search history.

(56) References Cited

U.S. PATENT DOCUMENTS

| 4,010,012 | A | | 3/1977 | Griffin, III et al. |
| 4,924,695 | A | | 5/1990 | Kolpak |
| 5,100,699 | A | | 3/1992 | Roeser |
| 5,211,842 | A | * | 5/1993 | Tuss ................... B01D 19/0015 166/75.12 |
| 5,251,488 | A | | 10/1993 | Haberman et al. |
| 5,394,339 | A | | 2/1995 | Jones |
| 6,032,539 | A | | 3/2000 | Liu et al. |
| 6,272,906 | B1 | | 8/2001 | Fleury et al. |
| 6,802,204 | B1 | | 10/2004 | Torkildsen |
| 6,847,898 | B1 | | 1/2005 | Chen et al. |
| 7,059,190 | B2 | | 6/2006 | Al-Ghamdi |
| 8,056,400 | B2 | | 11/2011 | Reintjes et al. |
| 8,245,572 | B2 | | 8/2012 | Birkett et al. |

(Continued)

FOREIGN PATENT DOCUMENTS

JP        2001150485 A  *  6/2001

*Primary Examiner* — Eric S. McCall
*Assistant Examiner* — Timothy P Graves
(74) *Attorney, Agent, or Firm* — James M. Duncan

(57) ABSTRACT

A method and apparatus includes devices for measuring the liquid rate, pressure, temperature and water cut from a production well, components and devices for diverting a liquid sample into a cylinder vessel, and components and devices for measuring parameters of the separated water phase of the liquid sample. The sample collection and analysis provides a means of significantly improving the accuracy of full-range water cut measurement by providing for improved calibration of a full range water cut meter.

12 Claims, 4 Drawing Sheets

(56) References Cited

U.S. PATENT DOCUMENTS 8,516,900 B2     8/2013   Pihlaja et al.
9,334,728 B2     5/2016   Marshall

* cited by examiner

OIL WELL GAUGING SYSTEM AND METHOD OF USING THE SAME

REFERENCE TO RELATED APPLICATIONS

This is a continuation-in-part application of currently pending U.S. application Ser. No. 15/166,910 filed on May 27, 2016, to which application the present inventors and Applicant claim domestic priority and which application is incorporated herein in its entirety by this reference.

BACKGROUND OF THE INVENTION

The present invention relates to production monitoring in general, and more specifically, to means and methods for monitoring the oil and water rates from a producing well.

There are three generally available methods for gauging oil producing wells: 1) multi-phase meters (MPMs) positioned directly in the production line to monitor the individual oil, water and gas rates; 2) gas/liquid separation and metering; 3) gas/oil/water separation and metering.

Well gauging systems that employ commercially available MPM technology have not yet achieved the necessary measurement accuracy and reliability to adequately handle variations in fluid composition, flow conditions and phase properties common to many oil field operations.

Gauging systems that employ gas/oil/water separation and metering devices actually separate the flow into gas, water-in-oil emulsion and water phases via velocity reduction and gravity segregation in a large pressure vessel or tank. The gas, emulsion and water rates exiting the separator are metered individually and the emulsion water cut is determined with a capacitance or impedance style meter. Properly designed three-phase systems employing commercial meters can provide accurate oil, water and gas rate measurements. However, three-phase systems have a relatively large footprint, can be very expensive to fabricate and costly to maintain.

Gas/liquid separation and metering systems are the most common means of gauging oil wells. The separator vessel size is typically smaller and the flow control and instrumentation are less complicated than three-phase systems. Gas and liquid rates exiting the separator are individually metered and the liquid stream water cut is measured via sample collection and analysis. Commercial full-range (i.e., 0% to 100%) water cut analyzers are often utilized in semi-automated or fully-automated gauging systems. However, some full-range water cut analyzers require stable, homogeneous flow conditions with a minimum or threshold velocity that is not often achievable during actual well operations. For water-continuous emulsions, water salinity can significantly affect the response characteristics of full-range water cut analyzers. Consequently, an independent means of measuring water salinity and a method for incorporating the resulting information into the analyzer are required to achieve accurate water cuts.

SUMMARY OF INVENTION

The main embodiments of the gauging system consists of a flow line equipped with instrumentation to continuously measure the liquid rate and water cut from a well in test mode. The system also contains a cylinder to periodically collect a liquid sample from the test line. The collected sample is allowed to settle for a predetermined time within the cylinder to obtain a sufficient quantity of water phase in the bottom portion of the cylinder.

During sample analysis mode, flow from the test line temporarily bypasses the full-range water cut analyzer. The separated water phase is displaced from the bottom of the cylinder and through a full-range water cut analyzer to establish key response characteristics and parameters needed to improve measurement accuracy. The remaining cylinder sample is subsequently displaced through the cut meter to provide a means of verifying that the analyzer is functioning properly as the fluid transitions from a water-continuous to oil-continuous emulsion.

Auxiliary instrumentation are located in the sample analysis line to measure additional fluid parameters and characteristics that are used to further refine water cut measurement accuracy. The cylinder sample collection and analysis process is repeated at specified intervals during each well test, as needed.

DETAILED DESCRIPTION OF EMBODIMENTS OF THE INVENTION

The features, aspects and advantages of this invention are described in more detail herein with reference to the drawings containing the system components and enumerated elements.

A well gauging system ("WGS") 100 is situated downstream of a gas/liquid separator at a single production well or at a multi-well production header. The WGS 100 can be skid mounted to facilitate installation or, alternatively, mounted on a trailer to provide for portable well testing. Produced fluids from a well are diverted through the WGS via manually operated or automated valves.

Figure 1:
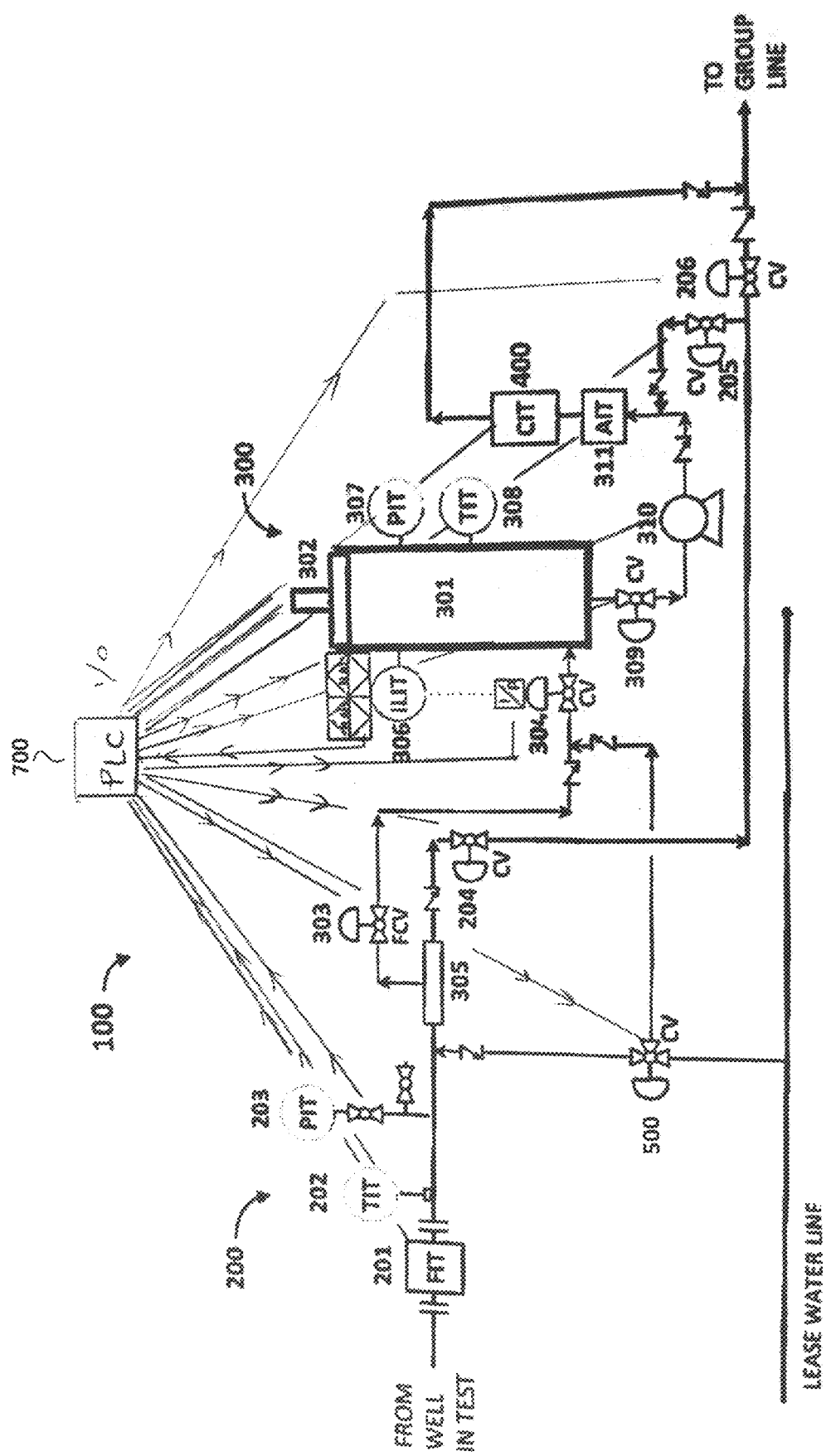
FIG. 1 illustrates a general embodiment of the well gauging system.

With reference to FIG. 1, the WGS 100 comprises a well test line component 200, a sample collection and analysis component 300, a full-range water cut analyzer component 400, a flush line component 500, a programmable logic controller 700 and a high speed data acquisition and analysis system that, in combination, significantly improve water cut measurement accuracy. The WGS 100 may further comprise one or more human machine interface screens for setting system operation modes and displaying measurement values, instrumentation status, alarms and shut-downs.

Figure 2:
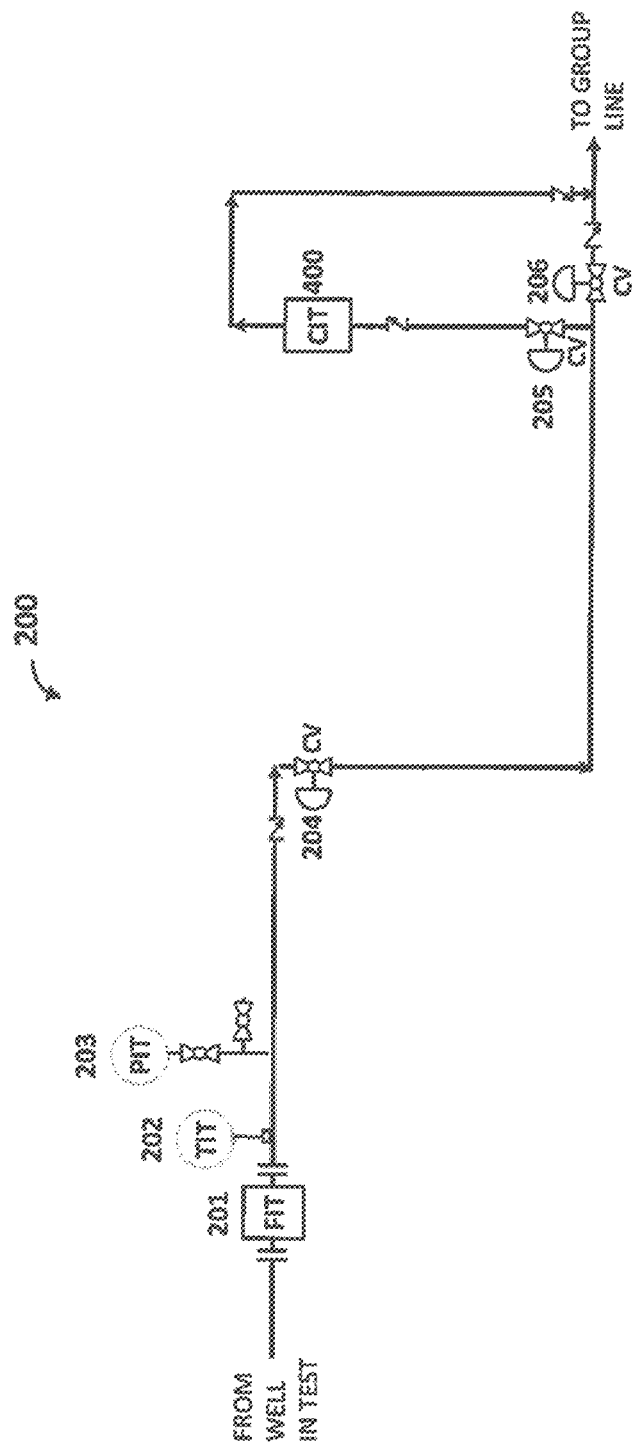
FIG. 2 illustrates an embodiment of a well test line component of the system.

The well test line component 200, an embodiment of which is depicted in FIG. 2, comprises a pipe which may have a variety of different diameters, such as 1 inch, 1½ inches, 2 inches or 3 inches. The pipe may have a constant diameter and be fabricated in an appropriate material for the application, such as steel. Well test line component 200 may further comprise a flow meter 201, a full-range water cut analyzer 400, temperature transmitter 202 and pressure transmitter 203. The well test line component further comprises control valves 204, 205 and 206 which are normally closed (i.e., fail-closed). When valves 204 and 205 are placed in the open position, produced liquids from the well under test are routed through the flow meter 201, transmitters 202 and 203 and water cut analyzer 400. Flow through water cut analyzer 400 is terminated when valve 205 is placed in the closed position and valve 206 placed in the open position.

Figure 3:
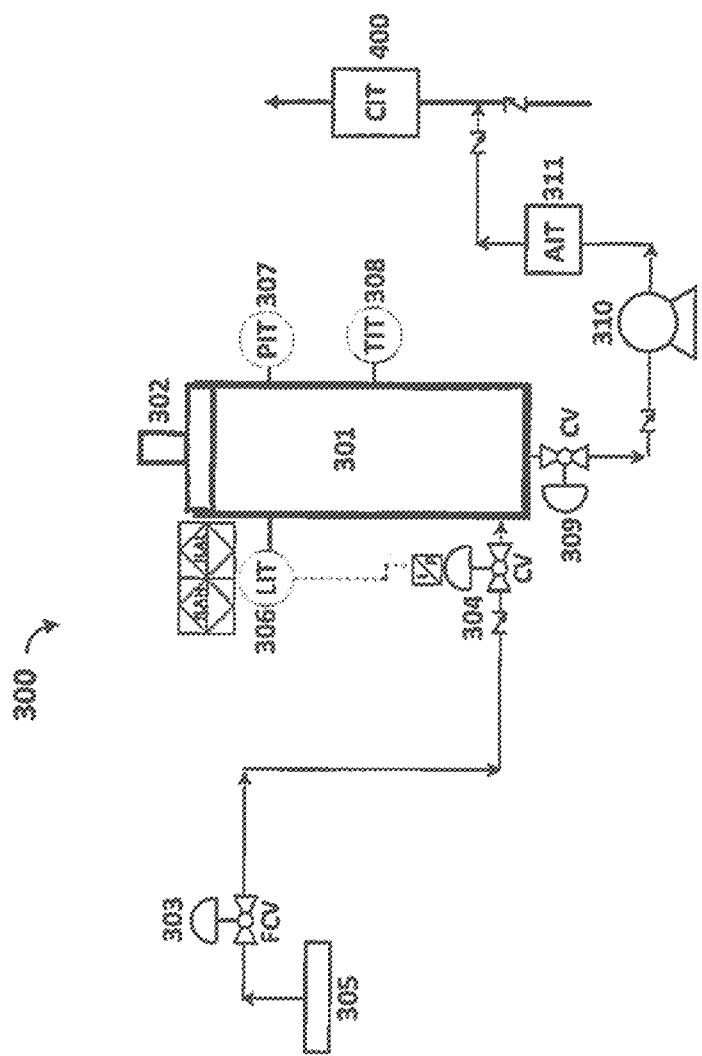
FIG. 3 illustrates an embodiment of a sample collection and analysis component of the system.

FIG. 3 illustrates an embodiment of a sample collection and analysis component 300 that may be used in the system. The sample collection and analysis component 300 comprises a sample collection vessel 301 which may be a cylinder fabricated with 316 stainless steel or aluminum and equipped with a piston 302 to improve fluid displacement from the cylinder. The piston 302 may be configured with a head and seals that efficiently clean the cylinder after each sample collection and analysis cycle. The piston 302 may be positioned at different locations within the cylinder by various means, including but not limited to hydraulic or electrical actuation.

The internal surface of the cylinder and piston 302 may be coated with a corrosion resistance material suitable for high temperature application. The size of the sample collection vessel 301 may depend on the oil density and viscosity under test conditions, and will typically be designed to hold a minimum of 3 gallons of sample fluid. When valves 303 and 304 are in the open position, a liquid extracting device 305 may be used to divert a portion of the liquid from the well test line component 200 into the sample collection vessel 301. The sample collection volume is monitored and controlled using a level indicating transmitter 306. Transmitters 307 and 308 monitor the cylinder sample temperature and pressure.

Once a predetermined sample volume has been collected, valves 303 and 304 are placed back in the closed position. The stationary cylinder sample is allowed to settle for predetermined time to obtain a sufficient quantity of water phase in the bottom portion of the cylinder.

During analysis mode, valve 309 is opened and the liquid sample is substantially displaced from the cylinder as the piston 302 moves from a "raised" position at the "top" of the cylinder to a "lowered" position at the "bottom" of the cylinder. Throughout this disclosure, the use of the terms "raised" and "top" should be understood to mean that the piston 302 being in the initial position prior to sample displacement and the terms "bottom" and "lowered" to mean that the piston 302 in its final position after the cylinder has been purged of the liquid sample. Various means may be utilized to augment phase separation of the liquid sample received with sample collection vessel 301. For example, sample collection vessel 301 may be equipped with either resistive heating coils or with a heat exchanger to either increase or decrease the temperature of the liquid sample. As another example, the sample collection vessel 301 may be equipped with sound wave emitters which may apply sonic energy to the liquid sample. As another example, chemicals may be introduced into the sample collection vessel 301 to augment phase separation. As another example, any combination of the previously identified mechanisms may be employed to augment phase separation.

In one embodiment, a pump 310 is positioned at an outlet of sample collection vessel 301. Pump 310 may be controlled by a variable frequency drive (VFD) and utilized to further displace the liquid sample through at least one auxiliary transducer 311, that measures supplemental fluid properties, and through a full-range water cut analyzer 400. Auxiliary transducer 311 may be of the type which utilizes speed of sound, density measurements, and/or electrical impedance measurements to ascertain a property of the fluid exiting the sample collection vessel 301. Likewise, full-range water cut analyzer 400 may be of the type which utilizes speed of sound, density measurements, and/or electrical impedance measurements to ascertain a property of the fluid flowing through the test line component. For example, the full range analyzers manufactured by PHASE DYNAMIC provide acceptable service. Auxiliary transducer 311 may be a full-range water cut analyzer identical to that of full range water cut analyzer 400.

Figure 4:
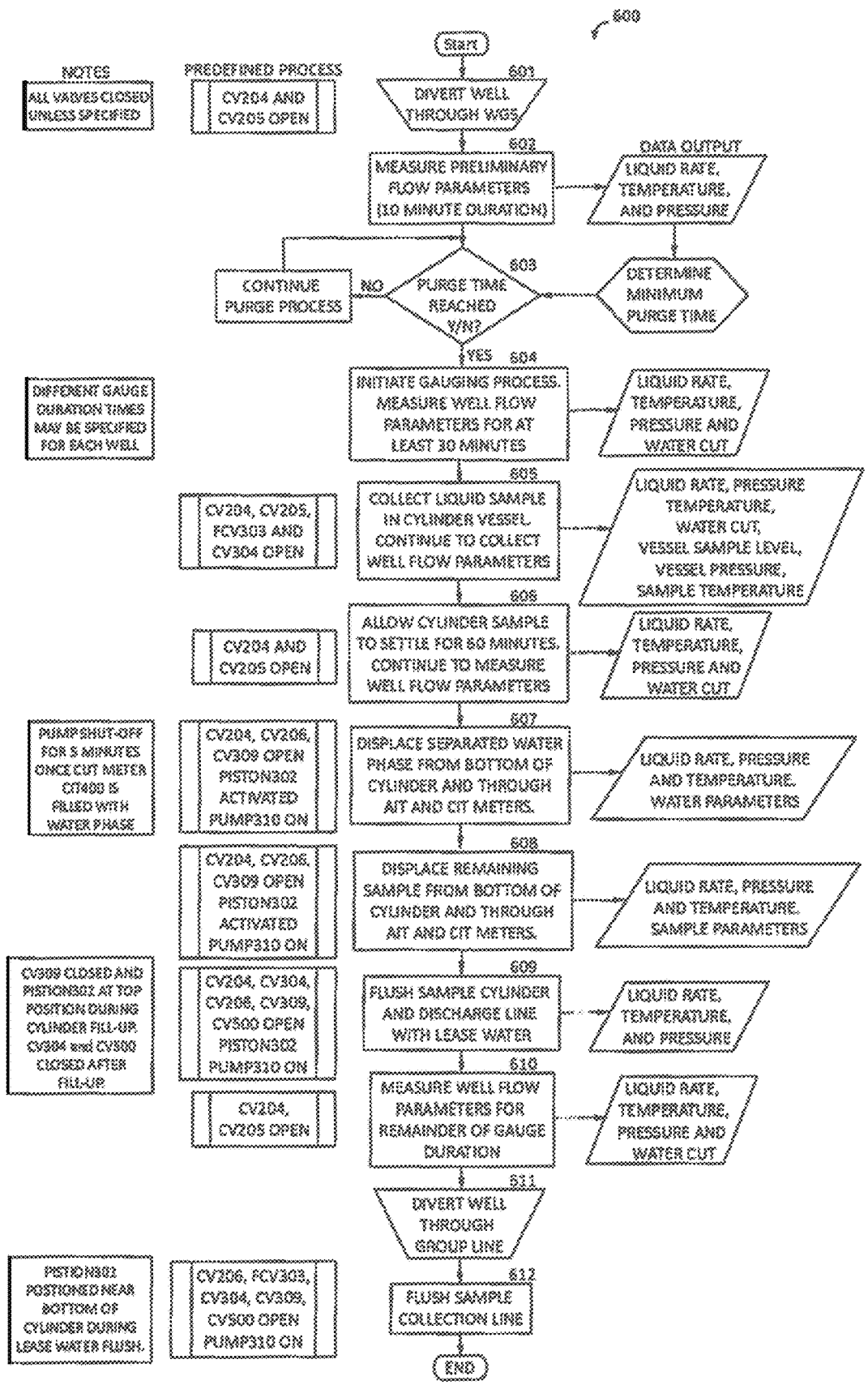
FIG. 4 illustrates an embodiment of an operational flow chart of the system.

With reference to FIGS. 1-3 and 4, a method 600 of testing and metering fluids produced from a well using the WGS are disclosed, with each step of the method identified by a reference number in the range 601-612. FIG. 4 illustrates embodiment 600 utilizing an operational flow chart for the WGS. In first step 601, the production well flow is first diverted through the WGS and preliminary liquid rate, pressure and temperature measurements are collected and utilized in step 602 to establish the appropriate purge time prior to commencement of the gauging process. At step 603, a determination is made whether the purge time has been reached. At step 604, the gauging process is initiated and liquid rate, temperature, pressure and water cut measurements are collected for at least 30 minutes.

At step 605, a sample of the production well's liquid stream is subsequently diverted into the cylinder vessel. Collection of the production well liquid rate, temperature, pressure and water cut measurements continue during the sampling process. At step 606, the cylinder sample is then allowed to settle for 60 minutes to achieve partial separation and obtain a sufficient quantity of water phase in the bottom portion of the cylinder. Collection of the production well liquid rate, temperature, pressure and water cut measurements continue during the sample settling process.

At step 607 the separated water is slowly displaced from the bottom of the cylinder and water parameter measurements are collected using auxiliary instrument 311 and full-range water cut analyzer 400. Water displacement is achieved through adjustment of the cylinder piston 302 position and setting the rate VFD-controlled pump 310 rate. Once the water cut analyzer 400 is completely filled with the water phase, the pump is shut-off and water parameter measurements are collected for an additional 5 minutes. At step 608 the remainder of the liquid sample is displaced through the bottom of the cylinder and parameter measurements are collected using the same means previously described. Collection of the production well liquid rate, temperature and pressure measurements continue during the sample analysis process.

At step 609 the sample cylinder and discharge line is subsequently flushed with lease water. Collection of the production well liquid rate, temperature and pressure measurements continue during the flush process. After the cylinder and discharge line have been flushed, collection of the production well water cut measurement is resumed for the remainder of the gauge duration.

Upon completion of the gauging process, at step 611 flow from production well is diverted through the group line. At step 612 the sample collection line is flushed with lease water. The WGS is now ready to test another production well.

While the above is a description of various embodiments of the present invention, further modifications may be employed without departing from the spirit and scope of the present invention. Thus the scope of the invention should not be limited according to these factors, but according to the following appended claims.

We claim:

1. A well gauging system comprising: a test line component configured to receive a flow of produced fluid from a well, the test line component comprising a flow meter, a first pressure transmitter, and a temperature transmitter;

a liquid sampling component comprising a sample extractor configured to collect a liquid sample from the flow of produced fluid flowing through the test line component, the liquid sampling component further comprising a collection vessel configured to receive the liquid sample, where the collection vessel comprises a fluid displacement piston, a liquid level transmitter, a second pressure transmitter and a collection vessel outlet;

a full range water cut analyzer component configured to selectively receive either a fluid flow from the collection vessel outlet or to receive at least a portion of the flow of produced fluid flowing through the test line component, wherein the fluid from the collection vessel outlet is utilized to calibrate the full range water cut analyzer; and a lease water flush component hydraulically connected to the test line component and the liquid sampling component, wherein the lease water flush component is configured to periodically release a portion of lease water to flush the test line component or the liquid sampling component.

2. The system of claim 1 wherein the liquid sampling component comprises an auxiliary transducer configured to detect a fluid property of a fluid flowing through the collection vessel outlet.

3. The system of claim 2 further comprising a programmable logic controller which receives input from the flow meter, the first pressure transmitter, the second pressure transmitter, the temperature transmitter, the liquid level transmitter, the auxiliary transmitter, and the full range water cut analyzer component, wherein the programmable logic controller controls the flow of the liquid sample to the liquid sampling component and controls the flow fluid from a pump outlet and the test line component to the full range water cut analyzer component.

4. The system of claim 1 wherein the liquid sample is substantially displaced from the collection vessel as the piston moves from a raised position to a lowered position.

5. The system of claim 1 wherein a pump is hydraulically connected to the vessel outlet, the pump comprising a pump outlet wherein the auxiliary transducer detects the fluid property from a fluid flowing through the pump outlet.

6. The system of claim 5 wherein the pump comprises a variable frequency drive.

7. The system of claim 1 wherein the liquid sample is retained within the collection vessel for a fixed period of time.

8. The system of claim 7 wherein the fixed period of time comprises a minimum of 30 minutes to a maximum of 60 minutes.

9. The system of claim 1 wherein the fluid from the collection vessel outlet is utilized to calibrate the full range water cut analyzer to the salinity of the produced fluids from the well.

10. A method of testing and metering fluids produced from a well for a test cycle utilizing the system of claim 1, the method comprising the steps of:

initiating a gauging process by collecting a plurality of measurements for a fixed period of time, wherein the plurality of measurements comprise liquid rate, temperature, pressure and water cut measurements ascertained from the full range water cut analyzer component;

diverting the liquid sample to the collection vessel;

allowing the liquid sample to settle within the collection vessel for a period from 30 minutes to 60 minutes resulting in a portion of separated water;

flowing the portion of separated water to the full range water cut analyzer component, wherein the portion of separated water is utilized to calibrate the full ranger water cut analyzer component;

flushing the collection vessel with lease water;

directing the flow from the well to flow through the full range water cut analyzer component through the end of the test cycle; and flushing the test line component with lease water.

11. The method of claim 10 further comprising a preliminary step of measuring flow rate, temperature and pressure prior to initiating the gauging process.

12. The method of claim 11 wherein a minimum purge time is determined from the preliminary step of measuring flow rate, temperature and pressure prior to initiating the gauging process.

* * * * *